United States Patent

Imanishi

[11] Patent Number: 6,043,060
[45] Date of Patent: Mar. 28, 2000

[54] NUCLEOTIDE ANALOGUES

[76] Inventor: Takeshi Imanishi, 2-18, Chiyogaoka 2-chome, Nara-shi, Nara 631-0045, Japan

[21] Appl. No.: 09/308,367
[22] PCT Filed: Nov. 18, 1997
[86] PCT No.: PCT/JP97/04187
  § 371 Date: May 18, 1999
  § 102(e) Date: May 18, 1999
[87] PCT Pub. No.: WO98/22489
  PCT Pub. Date: May 28, 1998

[30] Foreign Application Priority Data

Nov. 18, 1996 [JP] Japan .................................. 8-306585

[51] Int. Cl.[7] .......................... C07H 21/00; C07H 19/10; C07H 19/20
[52] U.S. Cl. .......................... 435/91.1; 435/89; 536/22.1; 536/23.1; 536/25.6
[58] Field of Search .................... 536/23.1, 27.1, 536/25.6, 26.1; 424/1.73

[56] References Cited

PUBLICATIONS

Christensen et al. A novel class of Oligonucleotide analogues containing 2'–0,3'0–C–linked [3.2.0]Bicyclioarabinocleoside monomers: Synthesis, Thermal Affinity Studies, and Molecular Modeling, JACS, vol. 120, pp. 5458–5463, 1998.

O–Yang et al. 4'–substituted Nucleosides as Inhibitors of HIV, Tet Lett. vol. 33, No. 1, pp. 41–44, 1992.

*Primary Examiner*—George C. Elliott
*Assistant Examiner*—Janet L. Epps
*Attorney, Agent, or Firm*—Browdy and Neimark

[57] ABSTRACT

An oligonucleotide analog or an antisense molecule, which is minimally hydrolyzable with an enzyme in vivo, has a high sense strand binding ability, and is easily synthesized, is provided. It is an oligo- or polynucleotide analog containing one or more monomer units being nucleotide analogs of the general formula:

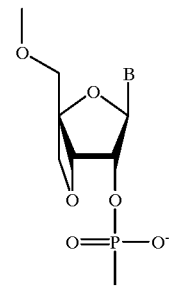

where B may be identical or different, and is a pyrimidine or purine nucleic acid base, or a derivative thereof.

3 Claims, 2 Drawing Sheets

NUCLEOTIDE ANALOGUES

CROSS REFERENCE TO RELATED APPLICATION

The present application is the national stage under 35 U.S.C. 371 of PCT/JP97/04187, filed Nov. 18, 1997.

TECHNICAL FIELD

This invention relates to a novel nucleotide analog, and more particularly, to a nucleotide analog suitable as an antisense molecule.

BACKGROUND ART

In 1978, it was reported for the first time that an antisense molecule inhibited influenza virus infection. Since then, reports have been issued that antisense molecules inhibited the expression of oncogenes and HIV infection. In recent years, antisense oligonucleotides have become one of the most promising pharmaceuticals, because they specifically control the expression of undesirable genes.

The antisense method is based on the idea of controlling a unidirectional flow called the central dogma, i.e., DNA→RNA→protein, by use of an antisense oligonucleotide.

When a naturally occurring oligonucleotide was applied to this method as an antisense molecule, however, it was hydrolyzed with enzymes in vivo, or its permeation through the cell membrane was not high. To solve these problems, numerous nucleic acid derivatives have been synthesized, and studies thereon have been conducted. Examples of synthesized derivatives include a phosphorothioate having a sulfur atom substituting for an oxygen atom on the phosphorus atom, and a methylphosphonate having a substituting methyl group. Recently, molecules in which the phosphorus atom has also been substituted with a carbon atom, or in which the ribose has been converted to an acyclic skeleton have been synthesized (F. Eckstein et al., *Biochem.*, 18, 592 (1979), P. S. Miller et al., *Nucleic Acids Res.*, 11, 5189 (1983), P. Herdewijn et al., *J. Chem. Soc. Perkin Trans.* 1, 1567 (1993), and P. E. Nielsen et al., *Science*, 254, 1497 (1991)).

All of the resulting derivatives, however, have been unsatisfactory in terms of in vivo stability or ease of oligonucleotide synthesis.

Under the circumstances, there has been a demand for the provision of a nucleotide analog for an antisense molecule which readily permeates through the cell membrane in vivo, which is minimally hydrolyzed with an enzyme, and the synthesis of which is easy.

DISCLOSURE OF THE INVENTION

The inventors of the present invention have designed a nucleic acid derivative with a modified sugar portion of a nucleic acid, which would be useful in the antisense method. They have synthesized the nucleic acid derivative, and confirmed its usefulness. The present invention will now be described.

A nucleotide analog of the present invention is an oligo- or polynucleotide analog containing one or more monomer units being nucleotide analogs of the following general formula:

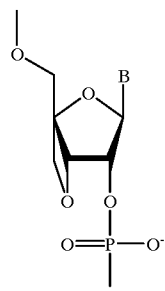

where B may be identical or different, and is a pyrimidine or purine nucleic acid base, or a derivative thereof.

This monomer unit is a nucleoside analog of the general formula:

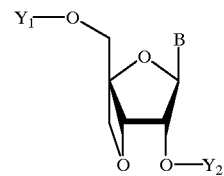

where B is a pyrimidine or purine nucleic acid base, or a derivative thereof, and $Y_1$ and $Y_2$ are identical or different, and is a hydrogen atom or a protective group for a hydroxyl group, provided that the protective group may be a publicly known group, preferably, an alkyl group, an alkenyl group, an alkynyl group, a cycloalkyl group, an aryl group, an acyl group, an aralkyl group, or a silyl group, or an amidite derivative thereof.

In the above formula, the alkyl group represents a straight chain or branched chain alkyl group with 1 to 20 carbon atoms. Its examples include methyl, ethyl, n-propyl, i-propyl, n-butyl, t-butyl, pentyl, hexyl, heptyl, octyl, nonyl and decyl.

The alkenyl group represents a straight chain or branched chain alkenyl group with 2 to 20 carbon atoms. Its examples include vinyl, allyl, butenyl, pentenyl, geranyl, and farnesyl.

The alkynyl group represents a straight chain or branched chain alkynyl group with 2 to 20 carbon atoms. Its examples include ethynyl, propynyl, and butynyl.

The cycloalkyl group represents a cycloalkyl group with 3 to 8 carbon atoms, and includes, for example, cyclopropyl, cyclobutyl, cyclopentyl, cyclohexyl, cycloheptyl, and cyclooctyl. Another example is a heterocyclic group in which one or more arbitrary methylene groups on the ring of the cycloalkyl group have been substituted by an oxygen atom, a sulfur atom, or an alkyl-substituted nitrogen atom. It is, for instance, a tetrahydropyranyl group.

The aryl group refers to a monovalent substituent formed by removing one hydrogen atom from an aromatic hydrocarbon group. Its examples include phenyl, tolyl, xylyl, biphenyl, naphthyl, anthryl, and phenanthryl. The carbon atom on the ring of the aryl group may be substituted by one or more of a halogen atom, a lower alkyl group, a hydroxyl group, an alkoxyl group, an amino group, a nitro group, and a trifluoromethyl group. The substituent in this case is, for example, a halogen atom, a hydroxyl group, an amino group, an alkoxy group, or an aryloxy group.

As the acyl group, acetyl, formyl, propionyl, benzoyl, and benzyloxycarbonyl can be exemplified.

An example of the silyl group is a trialkylsilyl group, preferably trimethylsilyl, triethylsilyl, triisopropylsilyl, t-butyldimethylsilyl or t-butyldiphenylsilyl, and more preferably trimethylsilyl.

The aralkyl group refers to an aromatic hydrocarbon-substituted alkyl group, preferably, benzyl or trityl. Each aromatic ring in this case may be substituted. An even more preferred aralkyl group is 4,4'-dimethoxytrityl (DMTr).

The pyrimidine or purine nucleic acid base in the present invention refers to thymin, uracil, cytosine, adenine, guanine, or a derivative thereof.

BEST MODE FOR CARRYING OUT THE INVENTION

Figure 1:
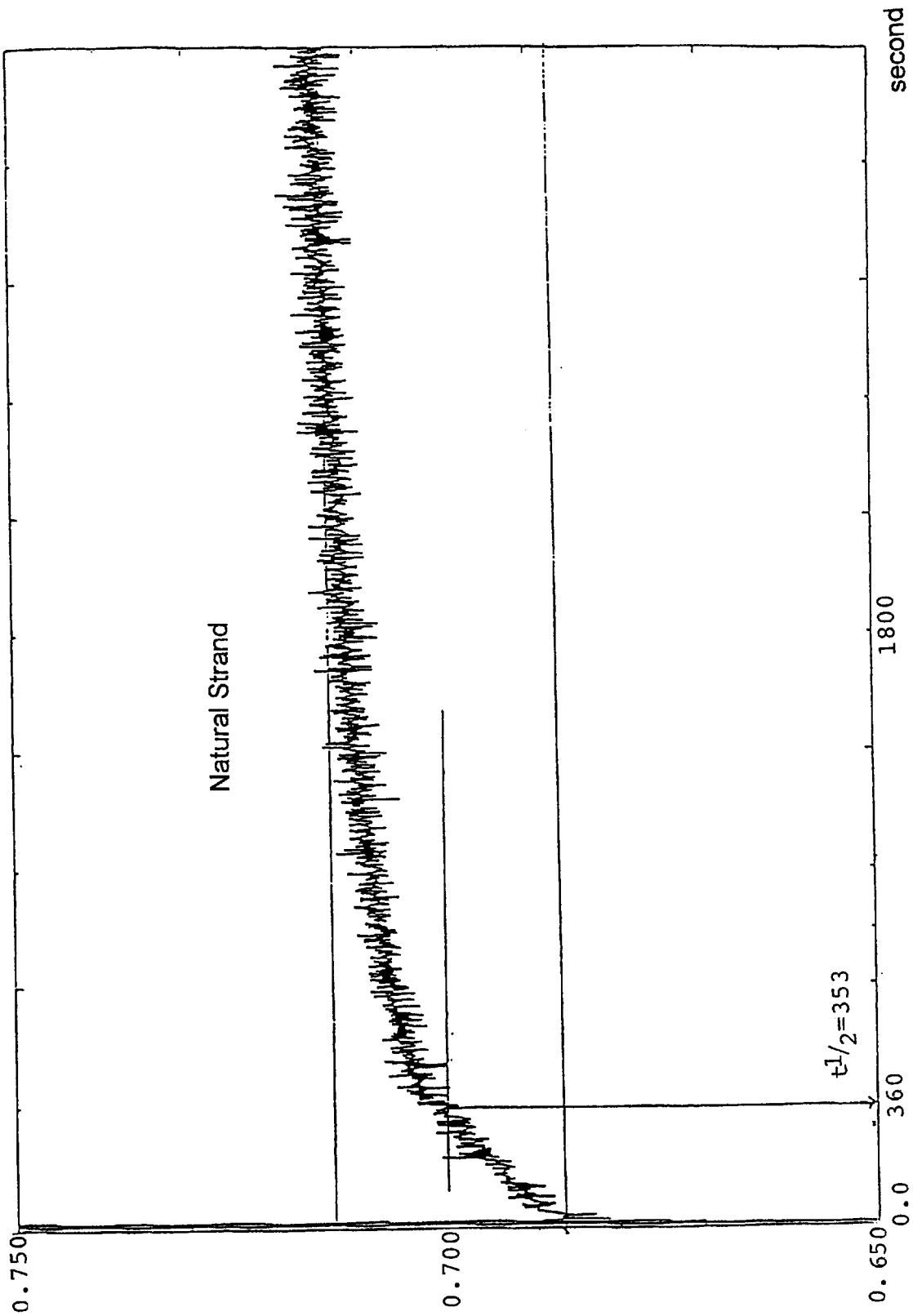
FIG. 1 is a chart showing the time course of the ultraviolet absorption (260 nm) of a naturally occurring oligonucleotide degraded with an exonuclease.

The nucleotide analog of the present invention can be synthesized in the manner described below. To simplify explanation, a compound in which B in the formula denotes uracil is taken as an example.

(1) Synthesis of monomer unit

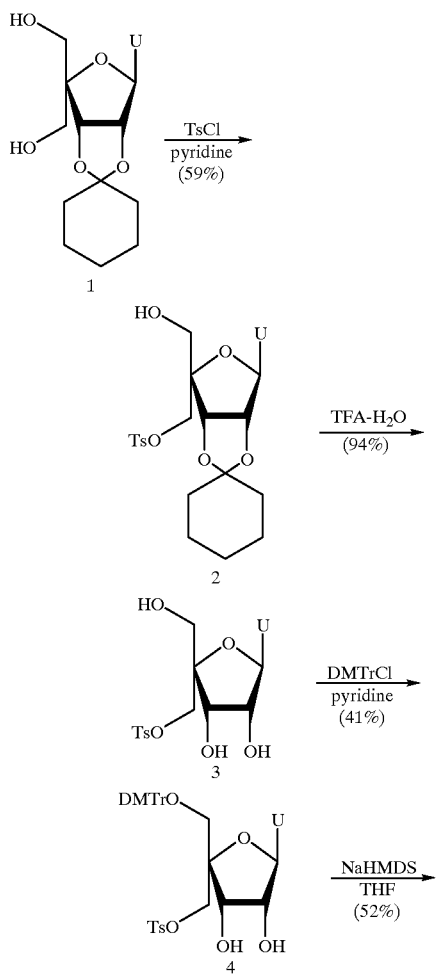

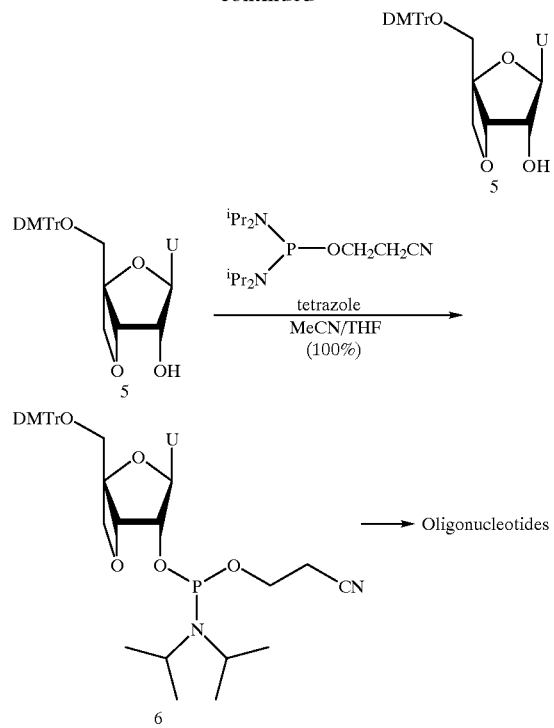

A compound known in the literature, 2',3'-O-cyclohexylidene-4'-(hydroxymethyl)uridine (1), is reacted with p-toluenesulfonyl chloride to obtain compound 2. Then, this compound is stirred in TFA-H$_2$O to obtain compound 3,4'-(p-toluenesulfonyloxymethyl)uridine.

Compound 3 is reacted with 4,4'-dimethoxytrityl chloride to obtain compound 4 having a protected hydroxyl group at the 5'-position. Compound 4 is further reacted with NaH-MDS to obtain compound 5,5'-O-(4,4'-dimethoxytrityl)-3'-O,4'-methanouridine.

(2) Synthesis of oligonucleotide analog

Compound 5 is reacted with 2-cyanoethyl N,N,N',N'tetraisopropylphosphorodiamidite to obtain an amidite compound (compound 6), from which various antisense oligomer analogs are synthesized using a DNA synthesizer. Then, the resulting antisense oligomer analog is purified using a reversed phase column. The purity of the purified compound is analyzed by reversed phase HPLC, whereby the formation of a purified oligonucleotide analog can be confirmed.

At least one monomer unit as compound 5 can be contained in the oligonucleotide analog. Alternatively, the monomer units may be present at two or more locations in the oligonucleotide analog in such a manner as to be separated from each other via one or more naturally occurring nucleotides. The present invention makes it possible to synthesize an antisense molecule incorporating a necessary number of the nucleotide analogs of the invention (a necessary length of the nucleotide analog) at a necessary location. The length of the entire nucleotide analog is 2 to 50, preferably 10 to 30, nucleoside units.

Such an antisense molecule is minimally degradable by an endonuclease as well as an exonuclease, and can be existent in vivo for a long time after administration. This antisense molecule forms a double helix together with a sense strand RNA to inhibit the formation (translation) of a pathogenic in vivo component (protein), or forms a triple helix in combination with double-stranded DNA to inhibit transcription to MRNA. The antisense molecule may also inhibit the proliferation of an infecting virus. In light of these findings, an antisense molecule using the nucleotide analog of the present invention is expected to find use in the from of drugs, including antineoplastics and antivirals, for the treatment of diseases by inhibiting the actions of genes.

The antisense molecule using the nucleotide analog of the invention can be formulated into parenteral preparations by incorporating conventionalauxiliaries such as buffers and/or stabilizers. For topical application, it may be blended with pharmaceutical carriers in common use to prepare ointments, creams, liquids or plasters.

Synthesis of the nucleotide analog of the present invention will be described in more detail by way of the following Examples.

EXAMPLE 1
Synthesis of monomer unit (1) Synthesis of 2',3'-O-cyclohexylidene-4'-(p-toluenesulfonyloxymethyl)uridine (compound 2)

To an anhydrous pyridine (13.5 ml) solution of compound 1 (956 mg, 2.70 mmols) known in the literature (G. H. Jones et al., *J. Org. Chem.*, 44, 1309(1979)), p-toluenesulfonyl chloride (771 mg, 4.05 mmols) was added at room temperature in a stream of nitrogen. The mixture was stirred for 5 hours at 60° C. To the reaction mixture, a saturated sodium bicarbonate solution was added, whereafter the reaction system was extracted with benzene 3 times. The organic phase was washed once with a saturated sodium chloride solution, and dried over anhydrous $MgSO_4$. The solvents were distilled off under reduced pressure, and the residue was subjected to azeotropy with benzene 3 times. The resulting crude product was purified by silica gel column chromatography ($CHCl_3$:MeOH=15:1), and reprecipitated from benzene/hexane to obtain a white powder (compound 2) (808 mg, 1.59 mmols, 59%).

m.p. 104–106° C. (benzene/hexane).

IR (KBr): $\nu_{max}$ 3326, 2929, 2850, 1628, 1577, 1544, 1437, 1311, 1244 $cm^{-1}$.

$^1$H-NMR (acetone-$d_6$): δ 1.45–1.67 (10H, m, cyclohexyl-), 2.45 (3H, s, φ-$CH_3$), 3.71 (2H, ABq, J=11.5 Hz, C5'-$H_2$), 4.20 (2H, ABq, J=10.5 Hz, C4'-$CH_2$OTs), 4.92 (1H, d, $J_{2'3'}$=6.4 Hz, C3'-H), 5.05, 5.06 (1H, dd, $J_{1'2'}$=3.7 Hz, $J_{2'3'}$=6.4 Hz, C2'-H), 5.60 (1H, d, $J_{4'5'}$=7.3 Hz, C4'-H), 5.75 (1H, d, $J_{1'2'}$=3.7 Hz, C1'-H), 7.48 (2H, d, J=8.2 Hz, φ), 7.77 (1H, d, $J_{4'5'}$=7.8 Hz, C5-H), 7.81 (2H, d, J=8.2 Hz, φ), 10.10 (1H, s, N$H$).

$^{13}$C-NMR (acetone-$d_6$): δ 21.5, 24.1, 24.5, 25.5, 34.8, 36.9, 63.5, 69.7, 82.5, 84.7, 87.8, 92.9, 102.9, 115.4, 128.8, 130.8, 133.9, 142.7, 145.9, 151.3, 163.5.

Mass (EI): m/z 481 ($M^+$-$H_2O$).

Anal. Calcd. for $C_{23}H_{28}N_2O_9S \cdot \frac{1}{3}H_2O$: C, 53.69;H, 5.61;N, 5.44;S, 6.22. Found: C, 53.99;H, 5.48;N, 5.42;S, 6.10.

(2) Synthesis of 4'-(p-toluenesulfonyloxymethyl)uridine (compound 3)

The above compound 2 (107 mg, 0.21 mmol) was stirred in TFA-$H_2O$ (98:2, 1 ml) for 10 minutes at room temperature. The reaction mixture was distilled off under reduced pressure, and ethanol was added to the residue, followed by performing azeotropy 3 times. The resulting crude product was purified by silica gel column chromatography ($CHCl_3$:MeOH=10:1) to obtain a white powder (compound 3) (85.0 mg, 0.20 mmol, 94%).

m.p. 119–120° C.

IR (KBr): $\nu_{max}$ 3227, 3060, 2932, 2837, 1709, 1508, 1464, 1252, 978, 835, 763, 556 $cm^{-1}$.

$^1$H-NMR (acetone-$d_6$): δ 2.31 (3H, s, φ-$CH_3$), 2.84 (3H, s, O$H$), 3.71 (2H, s, C5'-$H_2$), 4.13, 4.20 (2H, ABq, J=10.9 Hz, C4'-$CH_2$OTs), 4.28, 4.31 (1H, dd, $J_{1'2'}$=8.6 Hz, $J_{2'3'}$=5.6 Hz, C2'-H), 4.36 (1H, d, $J_{2'3'}$=5.6 Hz, C3'-H), 5.54 (1H, d, $J_{4'5'}$=7.9 Hz, C4-H), 5.75 (1H, d, $J_{1'2'}$=6.6 Hz, C1'-H), 7.32 (2H, d, J=7.9 Hz), 7.67 (2H, d, J=8.2 Hz), 7.70 (1H, d, $J_{4'5'}$=8.3 Hz, C5-H), 10.14 (1H, s, NH).

$^{13}$C-NMR (acetone-$d_6$): δ 21.5, 63.7, 70.8, 72.7, 74.6, 86.8, 88.8, 103.1, 128.8, 130.7, 133,9, 141.7, 145.8, 151.8, 163.9.

Mass (EI): m/z 256 ($M^+$-OTs).

(3) Synthesis of 5'-O-(4,4'-dimethoxytrityl)-4'-(p-toluenesulfonyloxymethyl)uridine (compound 4)

To the above compound 3 (1.13 g, 2.64 mmols), anhydrous pyridine was added, and azeotropy was performed 3 times to form an anhydrous pyridine solution (14.5 ml). Then, 4,4'-dimethoxytrityl chloride (1.07 g, 3.17 mmols) was added at room temperature in a stream of nitrogen, and the mixture was stirred for 16 hours at room temperature.

To the reaction mixture, a saturated sodium bicarbonate solution was added, whereafter the reaction system was extracted with $CH_2Cl_2$ 3 times. The organic phase was washed once with a saturated sodium chloride solution, and dried over anhydrous $MgSO_4$. The solvents were distilled off under reduced pressure, and the residue was subjected twice to azeotropy with benzene. The resulting crude product was purified by silica gel column chromatography ($CHCl_3$:$Et_3$N:MeOH=60:2:0→60:2:4), and reprecipitated from ethanol/hexane to obtain a white powder (compound 4) (868 mg, 1.06 mmols, 41%).

m.p. 104–105° C. ($Et_2O$/hexane).

IR (KBr): $\nu_{max}$ 3396, 2937, 2737, 2675, 2493, 1691, 1474, 1397, 1173, 1035 $cm^{-1}$.

$^1$H-NMR (acetone-$d_6$): δ 2.41 (3H, s, φ-$CH_3$), 3.22, 3.33 (2H, ABq, J=9.9Hz, C5'-$H_2$), 3.79 (6H, s, p-O$CH_3$-φ), 4.29 (1H, dd, $J_{1'2'}$=6.3 Hz, $J_{2'3'}$=5.6 Hz, C2'-H), 4.34, 4.41 (2H, ABq, J=11.2 Hz, C4'-$CH_2$OTs), 4.40 (1H, d, $J_{2'3'}$=5.6 Hz, C3'-H), 5.35 (1H, d, $J_{4'5'}$=8.3 Hz, C4-H), 5.82 (1H, d, $J_{1'2'}$=6.3 Hz, C1'-H), 6.89 (4H, d, J=8.9 Hz, p-$CH_3$O-φ), 7.26–7.41 (7H, m), 7.43 (1H, d, $J_{4'5'}$=8.3 Hz, C5-H), 7.70 (2H, d, J=8.3 Hz).

$^{13}$C-NMR (acetone-$d_6$): δ 21.6, 55.5, 64.6, 70.7, 72.7, 74.3, 85.8, 87.8, 88.9, 102.8, 114.0, 127.7,128.7, 128.8, 130.7, 130.9, 131.0, 133.9, 141.1, 145.5, 151.4, 159.7, 163.3.

Anal. Calcd. for $C_{38}H_{38}N_2O_{11}S \cdot \frac{1}{3}H_2O$: C, 61.95;H, 5.29;N, 3.80;S, 4.34. Found: C, 62.37;H, 5.26;N, 3.60;S, 4.15.

(4) Synthesis of 5'-O-(4,4'-dimethoxytrityl)-3'-O,4'-methanouridine (compound 5)

To compound 4 (735 mg, 0.90 mmol) in anhydrous THF (11.1 ml), an anhydrous benzene solution (4 ml) of NaHMDS (8.96 mmols) was added at room temperature in a stream of nitrogen, and the mixture was stirred for 48 hours at room temperature. To the reaction mixture, a saturated sodium bicarbonate solution was added, whereafter the reaction system was extracted with $CH_2Cl_2$ 3 times. The organic phase was washed once with a saturated sodium chloride solution, and dried over anhydrous $MgSO_4$.

The solvents were distilled off under reduced pressure, and the resulting crude product was purified by silica gel column chromatography ($CHCl_3$:$Et_3$N:MeOH=60:2:0→60:2:4). The purified product was reprecipitated from ethanol/hexane to obtain a white powder (compound 5) (261 mg, 0.47 mmol, 52%).

m.p. 120–121° C. ($Et_2O$/hexane).

IR (KBr): $\nu_{max}$ 3395, 3222, 3062, 2930, 1693, 1508, 1461, 1385, 1298, 1252, 1177, 1034 $cm^{-1}$.

$^1$H-NMR (acetone-$d_6$): δ 2.92 (1H, br s, O$H$), 3.47, 3.51 (2H, ABq, J=10.3Hz, C5'-$H_2$), 3.85 (6H, s, p-O$CH_3$-φ), 4.36

(1H, dd, $J_{1'2'}$=4.3 Hz, $J_{2'3'}$=4.3 Hz, C2'-H), 4.52, 4.83 (2H, ABq, J=7.7 Hz, C4'-$\underline{CH}_2$O-), 5.11 (1H, d, $J_{2'3'}$=4.3 Hz, C3'-H), 5.57 (1H, d, $J_{4'5'}$=7.7 Hz, C4-H), 6.51 (1H, d, $J_{1'2'}$=7.7 Hz, C1'-H), 6.96 (4H, d, J=8.6 Hz, p-CH$_3$O-φ), 7.39–7.41 (7H, m, φ), 7.52 (2H, d, J=5.1 Hz, φ), 7.71 (1H, d, $J_{4'5'}$=8.6 Hz, C5-H).

$^{13}$C-NMR (acetone-d$_6$): δ 55.4, 64.1, 75.5, 79.0, 85.5, 86.2, 87.1, 88.8, 103.3, 113.7, 113.9, 127.6, 128.4, 128.6, 128.8, 129.9, 130.9, 131.1, 136.3, 136.4, 141.2, 145.7, 151.6, 159.6, 163.4.

Mass (EI): m/z 558 (M$^+$), 303 (DmTr$^+$), 256 (M$^+$-DmTr), 227 (M$^+$-DmTrOCH$_2$).

(5) Synthesis of 2'-O-[2-cyanoethoxy(diisopropylamino) phosphino]-5'-O-(4,4'-dimethoxytrityl)-3'-O,4'-methanouridine (compound 6)

Compound 5 (261 mg, 0.47 mmol) and diisopropylammoniumtetrazolide (39.9 mg, 0.23 mmol) were subjected to azeotropy with anhydrous CH$_3$CN 3 times, and then converted into a solution in anhydrous CH$_3$CN-anhydrous THF (5:1, 10 ml). Then, 2-cyanoethyl-N,N,N',N'-tetraisopropylphosphorodiamidite (0.18 ml, 0.56 mmol) was added in a stream of nitrogen, and the mixture was stirred for 30 minutes at room temperature.

The solvents were distilled off under reduced pressure, and the resulting crude product was purified by silica gel column chromatography (anhydrous AcOEt:Et$_3$N=100:4). Then, the purified product was reprecipitated from anhydrous diethyl ether/hexane to obtain a white powder (compound 6) (340 mg, 0.47 mmol, 100%).

m.p. 94–96° C. (Et$_2$O/hexane).

IR (KBr): $v_{max}$ 2966, 2252, 2049, 1697, 1607, 1509, 1460, 1298, 1253, 1038 cm$^{-1}$.

$^{31}$P-NMR (acetone-d$_6$): δ 150.8, 151.2.

EXAMPLE 2

Synthesis of oligonucleotide analogs

| | |
|---|---|
| 5'-d(GCG-X-TTTTTGCT)-3' | (XT5; SEQ ID NO:1) |
| 5'-d(GCGTT-X-TTTGCT)-3' | (T2XT3; SEQ ID NO:2) |
| 5'-d(GCGTTT-X-TTGCT)-3' | (T3XT2; SEQ ID NO:3) |
| 5'-d(GCGTTTTT-X-GCT)-3' | (T5X; SEQ ID NO:4) |
| 5'-d(GCG-X-X-TTTTGCT)-3' | (X2T4; SEQ ID NO:5) |
| 5'-d(GCGTT-X-X-TTGCT)-3' | (T2X2T2; SEQ ID NO:6) |
| 5'-d(GCGTTTT-X-X-GCT)-3' | (T4X2; SEQ ID NO:7) |
| 5'-d(GCG-X-X-X-X-X-X-GCT)-3' | (X6; SEQ ID NO:8) |

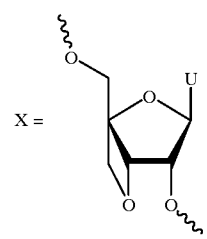

(1) Synthesis of 5'-GCGXTTTTTGCT-3'(XT5; SEQ ID NO:1)

A dimethoxytrityl group (DMTr group) of 5'-O-dimethoxytritylthymidine (0.2 μmol) having a 3'-hydroxyl group bound to a support was deprotected with trichloroacetic acid. Its 5'-hydroxyl group was condensed with 5'-O-dimethoxytrityldeoxycytidine-2-cyanoethylphosphoamidite derivative by use of tetrazole. The unreacted 5'-hydroxyl group was acetylated with acetic anhydride, 4-dimethylaminopyridine, and 2,4,6-collidine, and then the phosphorus was oxidized with iodine, 2,4,6-collidine and water.

Similarly, deprotection, condensation, acetylation and oxidation were repeated. (A four-membered ring amidite derivative was also usable similar to other amidite derivatives.) The last 5'-O-dimethoxytrityldeoxyguanosine-2-cyanoethylphosphoamidite derivative was condensed, and oxidized. The resulting 12-meric oligomer (the steps until formation of this product were performed by Pharmacia's DNA synthesizer, Gene Assembler Plus) was cleaved from the support by use of 1 ml of concentrated aqueous ammonia. At the same time, the cyanoethyl group was detached from the phosphorus, and the protective groups for the adenine, guanine and cytosine were also removed.

The resulting 5'-O-dimethoxytrityloligonucleotide was rid of the DMTr groups by use of 5 ml of trifluoroacetic acid on a reversed phase column (Millipore, Oligo-Pak™SP), and further purified to obtain the desired 5'-GCGXTTTTTGCT-3' (XT5) (0.02 mmol, 10%). The purity of the resulting oligonucleotide analog was confirmed by reversed phase HPLC.

(2) Synthesis of 5'-GCGTTXTTTGCT-3'(T2XT3; SEQ ID NO:2)

The desired 5'-GCGTTXTTTGCT-3'(T2XT3; SEQ ID NO:2) (0.04 mmol, 20%) was obtained in the same manner as in (1).

(3) Synthesis of 5'-GCGTTTXTTGCT-3'(T3XT2; SEQ ID NO:3)

The desired 5'-GCGTTTXTTGCT-3'(T3XT2; SEQ ID NO:3) (0.63 mmol, 15%) was obtained in the same manner as in (1).

(4) Synthesis of 5'-GCGTTTTTXGCT-3'(T5X; SEQ ID NO:4)

The desired 5'-GCGTTTTTXGCT-3'(T5X; SEQ ID NO:4) (0.02 mmol, 10%) was obtained in the same manner as in (1).

(5) Synthesis of 5'-GCGXXTTTTGCT-3'(X2T4; SEQ ID NO:5)

The desired 5'-GCGXXTTTTGCT-3'(X2T4; SEQ ID NO:5) (0.03 mmol, 15%) was obtained in the same manner as in (1).

(6) Synthesis of 5'-GCGTTXXTTGCT-3'(T2X2T2; SEQ ID NO:6)

The desired 5'-GCGTTXXTTGCT-3'(T2X2T2; SEQ ID NO:6) (0.03 mmol, 15%) was obtained in the same manner as in (1).

(7) Synthesis of 5'-GCGTTTTXXGCT-3'(T4X2; SEQ ID NO:7)

The desired 5'-GCGTTTTXXGCT-3'(T4X2; SEQ ID NO:7) (0.03 mmol, 15%) was obtained in the same manner as in (1).

(8) Synthesis of 5'-GCGXXXXXXGCT-3'(X6; SEQ ID NO:8)

The desired 5'-GCGXXXXXXGCT-3'(X6; SEQ ID NO:8) (0.03 mmol, 15%) was obtained in the same manner as in (1).

EXPERIMENTAL EXAMPLE 1

Measurement of melting temperature (Tm)

The Tm's of annealing products between oligomer strands (antisense strands), which were the various antisense molecules synthesized in Example 2, and the corresponding sense strands were measured to investigate the hybridizing ability of the antisenses.

Each sample solution (500 μL) with end concentrations of 100 mM NaCl, 10 mM sodium phosphate buffer (pH 7.2), 4 μM antisense strand, and 4 μM sense strand, respectively, was bathed in boiling water, and cooled to room temperature over the course of 10 hours. The sample solution was gradually cooled to 5° C., kept at 5° C. for a further period of 20 minutes, and then started to be measured, with a stream of nitrogen being passed through a cell chamber of a spectrophotometer (UV-2100PC, Shimadzu) for prevention of moisture condensation. The temperature was raised at a rate of 0.2° C./minute until 90° C., and the ultraviolet absorption at 260 nm was measured at intervals of 0.1° C. To prevent changes in the concentration with increases in the temperature, the cell was provided with a closure, and a drop of a mineral oil was applied to the surface of the sample solution during measurement.

The sequences of the antisense strands and the sense strands used in the measurements are tabulated below.

In the specification of this application, natural nucleotides are written as capital letters like T, C, A and G, and the analogs of the present invention as small letters like t, c, a and g, for convenience's sake.

| Oligonucleotide | $t_{1/2}$ (seconds) |
|---|---|
| Natural strand | 350 |
| X2 | 1390 |

Figure 2:
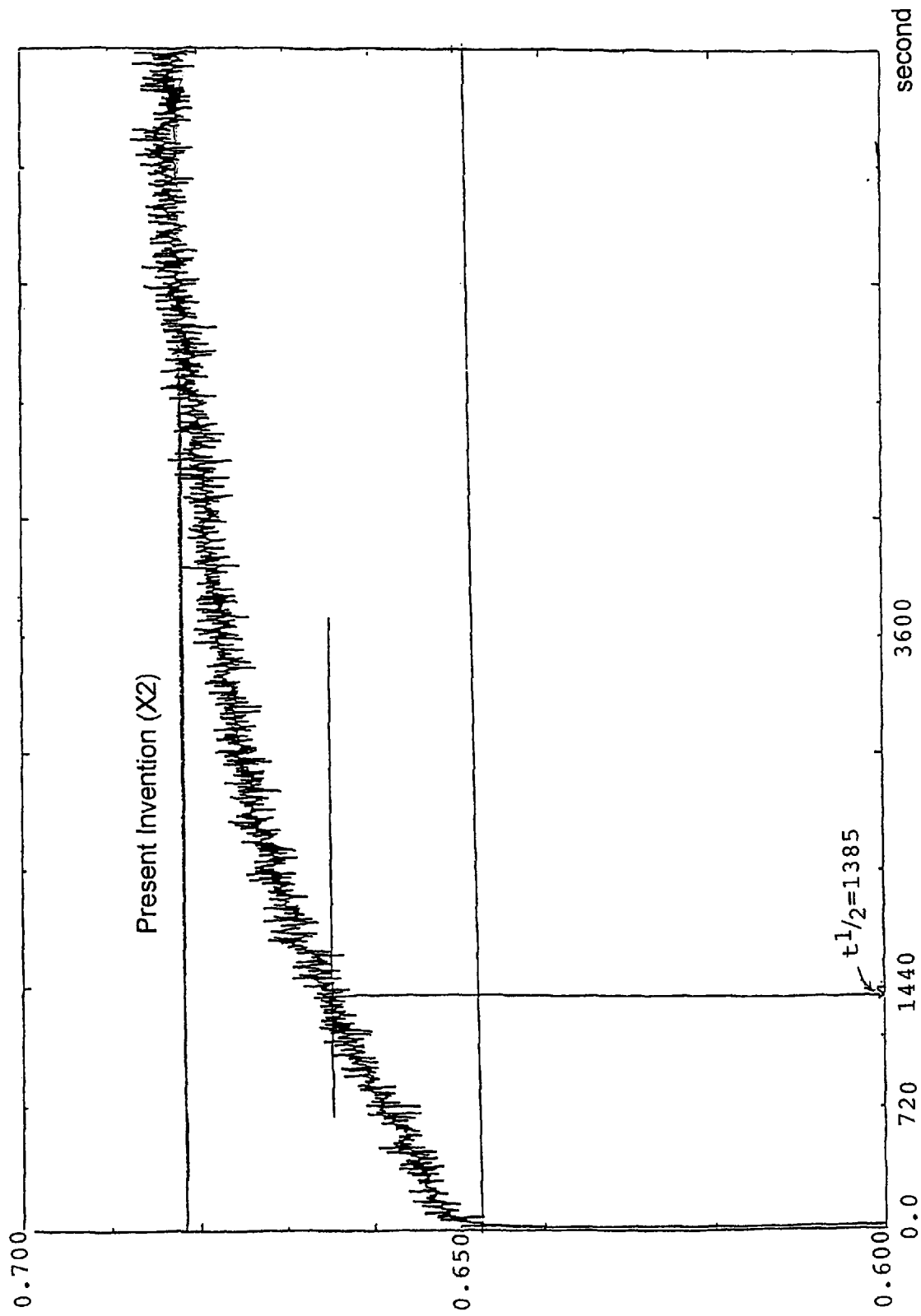
FIG. 2 is a chart showing the time course of the ultraviolet absorption (260 nm) of the oligonucleotide of the present invention (X2) degraded with an exonuclease.

Charts showing the time course of the ultraviolet absorption are presented as FIG. 1 (natural strand) and FIG. 2 (X2). The ultraviolet absorption reached a plateau in about 30 minutes for the natural strand, and about 90 minutes for X2, after initiation of the enzyme reaction.

| | Melting Temperatures of Oligomers | |
|---|---|---|
| Antisense strand | Sense strand<br>Complementary DNA<br>5'-AGCAAAAAACGC-3' (SEQ ID NO:12) | Complementary RNA<br>5'-AGCAAAAAACGC-3' (SEQ ID NO:12) |
| 5'-GCGTTTTTTGCT-3'<br>(T6; SEQ ID NO:11) | 47 | 45 |
| 5'-GCGXTTTTTGCT-3'<br>(XT5; SEQ ID NO:1) | 45 | |
| 5'-GCGTTXTTTGCT-3'<br>(T2XT3; SEQ ID NO:2) | 44 | 47 |
| 5'-GCGTTTXTTGCT-3'<br>(T3XT2; SEQ ID NO:3) | 43 | 44 |
| 5'-GCGTTTTTXGCT-3'<br>(T5X; SEQ ID NO:4) | 45 | |
| 5'-GCGXXTTTTGCT-3'<br>(X2T4; SEQ ID NO:5) | 34 | |
| 5'-GCGTTXXTTGCT-3'<br>(T2X2T2; SEQ ID NO:6) | 37 | 42 |
| 5'-GCGTTTTXXGCT-3'<br>(T4X2; SEQ ID NO:7) | 37 | 43 |
| 5'-GCGXXXXXXGCT-3'<br>(X6; SEQ ID NO:8) | N.D. | 28 |

N.D.: Not detected.

EXPERIMENTAL EXAMPLE 2

Measurement of enzyme resistance

A natural type oligonucleotide and a non-natural type oligonucleotide were examined for resistance to an exonuclease which degrades the oligonucleotide, starting at the 3'-terminal.

A buffer solution (0.003 U/ml, 400 µl) of a snake venom phosphodiesterase was mixed with a buffer solution (10 µM, 400 µl) of the oligonucleotide held at 37° C. for 15 minutes. Increases in the ultraviolet absorption (260 nm) due to the degradation of the oligomer were measured over time at 37° C. by means of SHIMADZU UV-2100PC. The buffer used comprised 0.1M Tris HCl (pH 8.6), 0.1M NaCl, and 14 MM $MgCl_2$, and was sufficiently degassed before measurement.

The sequences of the oligonucleotides used for measurement were as follows: 1

```
Natural strand: 5'-GTTTTTTTTTTC-3'(SEQ ID NO:9)
X2              5'-GTTTTTTTTXXC-3'(SEQ ID NO:10)
```

Measurement of half-life ($t_{1/2}$):

The ultraviolet absorption (260 nm) was measured at the start of measurement (t=0) and at the time when no increase in this parameter was noted. The average of the measured values was designated as the half-life ($t_{1/2}$). The results are given below.

I claim:

1. An oligo- or polynucleotide analog containing one or more monomer units of the general formula:

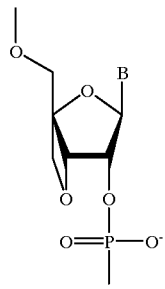

where B may be identical or different, and is a pyrimidine or purine nucleic acid base, or a derivative thereof.

2. The oligo- or polynucleotide analog of claim 1, comprising a total of 2 to 50 nucleotide units.

3. A nucleoside analog of the general formula:

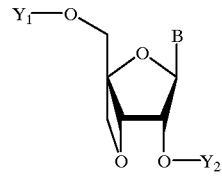

where B is a pyrimidine or purine nucleic acid base, or a derivative thereof, and $Y_1$ and $Y_2$ are identical or different, and is a hydrogen atom or a protective group for a hydroxyl group.

* * * * *

SEQUENCE LISTING

<160> NUMBER OF SEQ ID NOS: 12

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 1
gcgntttttg ct                                                               12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 2
gcgttntttg ct                                                               12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 3
gcgtttnttg ct                                                               12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 4
gcgtttttng ct                                                               12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 5 gcgnntttg ct                                                                12

<210> SEQ ID NO 6
<211> LENGTH: 12
<212> TYPE: DNA
<213> ORGANISM: Artificial Sequence

```
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 6
gcgttnnttg ct                                                              12

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 7
gcgttttnng ct                                                              12

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 8
gcgnnnnnng ct                                                              12

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic

<400> SEQUENCE: 9
gttttttttt ttc                                                             13

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
<220> FEATURE:
<223> OTHER INFORMATION: n is 3'-O, 4'-C-methylene uridine

<400> SEQUENCE: 10
gttttttttt nnc                                                             13

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 11 gcgtttttg ct                                                               12

<210> SEQ ID NO 12
<211> LENGTH: 12
<212> TYPE: DNA
```

```
<213> ORGANISM: Artificial Sequence
<220> FEATURE:
<223> OTHER INFORMATION: Description of Artificial Sequence: Synthetic

<400> SEQUENCE: 12
agcaaaaaac gc                                                          12
```